United States Patent [19]
Pak et al.

[11] Patent Number: 4,883,791
[45] Date of Patent: Nov. 28, 1989

[54] 25S,26-DIHYDROXYCHOLECALCIFEROL IN THE TREATMENT OF HYPERCALCITRIOLEMIC DISEASE STATES

[75] Inventors: Charles Y. C. Pak, Dallas, Tex.; Milan R. Uskokovic, Upper Montclair, N.J.; Joseph E. Zerwekh, Ovilla, Tex.

[73] Assignees: Board of Regents, The University of Texas System, Austin, Tex.; Hoffman-LaRoche, Inc., Nutley, N.J.

[21] Appl. No.: 99,191

[22] Filed: Sep. 21, 1987

[51] Int. Cl.$^4$ .............................................. A61K 31/59
[52] U.S. Cl. ..................................... 514/167; 514/891
[58] Field of Search ......................................... 514/167

[56] References Cited
U.S. PATENT DOCUMENTS
4,617,297 10/1986 Boris ..................................... 514/167

OTHER PUBLICATIONS

*Endocrinology*, vol. 121, No. 5, (1987) pp. 1671–1677, Joseph E. Zerwekh et al.
*Steroids*, vol. 32, No. 5 (Dec. 1978) pp. 577–587, Monique Thomasset et al.
Chemical Abstracts–vol. 90, 1979-115285X.
Chemical Abstracts–vol. 107, 1987-235294r.
Breslau et al., "Effects of Short Term Glucocoticoid Administration in Primary Hyperparathyroidism: Comparison to Sarcoidosis", J. Clin. Endocrinol, Metab. 58:824 (1982).

*Primary Examiner*—Paul E. Konopka
*Attorney, Agent, or Firm*—Arnold, White & Durkee

[57] ABSTRACT

The invention is directed to a method in the treatment of hypercalcitriolemic disease states which comprises administering an effective amount of 25S,26-dihydroxycholecalciferol to a host in need of such treatment.

7 Claims, No Drawings

25S,26-DIHYDROXYCHOLECALCIFEROL IN THE TREATMENT OF HYPERCALCITRIOLEMIC DISEASE STATES

BRIEF SUMMARY OF THE INVENTION

The invention is directed to a method for the treatment of hypercalcitriolemic disease states which comprises administering to a host in need of such treatment a therapeutically effective amount of 25S,26-dihydroxycholecalciferol.

DETAILED DESCRIPTION OF THE INVENTION

The invention comprises a method for the treatment of hypercalcitriolemic disease states which comprises the administration of an effective amount of 25S,26-dihydroxycholecalciferol to a host in need of such treatment. 25S,26-dihydroxycholecalciferol and its preparation are disclosed in Koizumi et al., J. Chem. Soc. Perkin Trans. I (1983) pages 1401-1410.

25S,26-dihydroxycholecalciferol lowers endogenous levels of 1α,25-dihydroxycholecalciferol, that is, it is hypocalcitriolemic.

Accordingly, 25S,26-dihydroxycholecalciferol can be administered to warm blooded animals in dosages that are in the range of about 20 to about 1000 micrograms/day for the treatment of hypercalcitriolemic disease states, such as, inoperative primary hyperparathyroidism, hypercalcemic granulomatous disease and certain forms of renal stone disease.

25S,26-dihydroxycholecalciferol can be administered orally, subcutaneously, intramuscularly, intravenously or intraperitoneally.

25S,26-dihydroxycholecalciferol can be formulated in compositions, such as, tablets, capsules, and the like or elixirs for oral administration or in sterile solutions or suspensions for parenteral administration. About 20-1000 micrograms of 25S,26-dihydroxycholecalciferol can be compounded with a pharmaceutically acceptable vehicle, carrier, excipient, binder, preservative, stabilizer, flavor and the like in the unit dosage as called for by accepted pharmaceutical practice. The amount of active substance in the foregoing compositions or preparations is in the range previously indicated.

Illustrative of the adjuvants which may be incorporated into capsules and the like are the following: a binder such as gum tragacanth, acacia, corn starch or gelatin; an excipient such as dihydroxyphosphate; a disintegrating agent such as corn starch, potato starch, algenic acid and the like; a lubricant such as magnesium stearate, a sweetening agent such as sucrose, lactose or saccharin; a flavoring agent such as peppermint, oil of wintergreen or cherry. Various other materials may be present as coating or to otherwise modify the physical form of a dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle, such as water for injection, a naturally occurring vegetable oil, such as, sesame oil, coconut oil, peanut oil, cottonseed oil, and the like, or synthetic fatty vehicles such as, ethyl oleate or the like. Buffers, preservatives, antioxidants and the like can be incorporated as required.

The useful activity of 25S,26-dihydroxycholecalciferol as an agent for the treatment of hypercalcitriolemic disease states can be demonstrated by the following test procedures.

MATERIALS AND METHODS

Animals

Adult female Sprague-Dawley rats weighing between 190-200 g were used in all studies and were purchased from Harlan (Houston, TX). The animals were housed in the animal resource facility and were fed a standard vitamin D-replete rat chow diet (2.0% calcium and 0.9% phorphorus, Tekland, Winfield, OH) ad lib. After four to five days of equlibration the animals were divided into appropriate study groups and injected subcutaneously each day with various doses of $25(S),26(OH)_2D_3$ or $1,25(OH)_2D_3$ metabolites. In some experiments, animals received both metabolites as two separate injections. Control animals received only vehicle (propylene glycol).

Vitamin D Metabolite Assay

Two ml of serum was obtained for each rat for measurement of $25(S),26(OH)_2D_3$, and $1,25\text{-}(OH)_2D_3$. After spiking the samples with approximately 1200 cpm of radiolabeled $25OHD_3$, $24,25\text{-}(OH)_2D_3$ and $1,25(OH)_2D_3$ and allowing the samples to equilibrate for 30 minutes, isolation of the vitamin D metabolites was accomplished as described in Bishop JE, Norman AW, Coburn JW, Roberts PA, Henry, HL 1980 "Determination of the concentration of 25-hydroxyvitamin D, 24,25-dihydroxyvitamin D and 1,25-dihydroxyvitamin D in a single two-milliliter plasma sample." Min Elect Metab 3: 181. Further separation and partial purification of the metabolites was effected with lipohilic Sephadex (Sigma, St. Louis, MO) liquid gel chromatography using a 9:1:1:0.015 (hexane:chloroform:methanol:$H_2O$) solvent system and a 10×1 cm gel bed as previously described by Eisman JA, Hamstra AJ, Kream BD, DeLuca HF, 1975, "A sensitive, precise and convenient method for determination of 1,25-dihydroxyvitamin D in human plasma." Arch Biochem Biophys 176: 235. This chromatographic system effectively separates 25OHD (5-11 ml) from the dihydroxy metabolites (14-30 ml). The trihydroxy metabolite $1,25,26(OH)_3D$ is eluted from the column by changing the solvent system to 8:2:2:0.015 (hexane:chloroform:methanol:$H_2O$) after elution of the dihydroxy metabolites and collecting the next 12 ml.

Final resolution and purification of the vitamin D metabolites was performed with high pressure liquid chromatography as previously described in Zerwekh et al., 1983, "Extra-renal production of 24,25-dihydroxyvitamin D in chronic renal failure during 25-hydroxyvitamin $D_3$ therapy." Kid Int. 23: 401 and Pak et al., 1982, "Effects of short-term glucocorticoid administration in primary hyperparathyroidism: comparison to sarcoidiosis J. Clin. Endrocrinol Metab. 54: 824. 25OHD was purified on a 5% 2-propanol in hexane solvent system. The three dihydroxyvitamin D metabolites were isolated and purified using an 11% 2-propanol in hexane solvent system. The assay of $25S,26\text{-}(OH)_2D$ was performed using the rat serum vitamin D binding protein assay system described in Haddad JG, Chyu KF 1971 "competitive protein binding assay for 25-hydroxycholecalciferol." J Clin Endocrinol Metab 33: 992. The assay of 1,25(OH)$_2$D was accomplished using the chick intestinal receptor protein.

TABLE 1

Effect of 25S,26(OH)$_2$D$_3$ Administration on 1,25(OH)$_2$D$_3$ Mediated Increases in Serum 1,25(OH)$_2$D$_3$

| Exp. No. | 25S,26(OH)$_2$D (ng/ml) | 1,25(OH)$_2$D (pg/ml) |
|---|---|---|
| 1. CONTROL | 1.9 ± 0.2 | 25 ± 3 |
| 1,25(OH)$_2$D$_3$[a] | 3.0 ± 0.8 | 206 ± 17 |
|  |  | ($p < 0.001$) |
| 25S,26(OH)$_2$D$_3$[b] | 295 ± 7 | 59 ± 3 |
| + | ($p < 0.001$) |  |
| 1,25(OH)$_2$D$_3$ |  |  |
| 2. CONTROL | 2.0 ± 0.2 | 23 ± 3 |
| 1,25(OH)$_2$D$_3$ | 3.20 ± 0.3 | 175 ± 52 |
|  |  | ($p = 0.006$) |
| 25S,26(OH)$_2$D$_3$ | 168 ± 14 | 46 ± 4 |
| + | ($p < 0.01$) |  |
| 1,25(OH)$_2$D$_3$ |  |  |
| 3. CONTROL | 1.20 ± 0.1 | 27 ± 4 |
| 1,25(OH)$_2$D$_3$ | 0.9 ± 0.3 | 180 ± 45 |
|  |  | ($p < 0.001$) |
| 25S,26(OH)$_2$D$_3$ | 236 ± 28 | 38 ± 6 |
| + | ($p < 0.006$) |  |
| 1,25(OH)$_2$D$_3$ |  |  |

Values in parenthesis represent p value of significant difference between dosed and control animals as determined by non-parametric analysis and Welch's approximation to the t test. All values expressed as mean ± SEM for seven rats per group.
[a]1,25(OH)$_2$D$_3$ administered subcutaneously at a dose of 0.15 μg/d/rat for three days
[b]25S,26(OH)$_2$D$_3$ administered subcutaneously for seven days at a dose of 20 μg/d/rat; on days 5, 6, and 7 both 25S,26(OH)$_2$D$_3$ and 1,25(OH)$_2$D$_3$ (0.15 μg/d/rat) were given as two separate injections.

As the above results demonstrate, 25S,26-dihydroxycholecalciferol is active in reducing serum concentrations of 1,25-dihydroxycholecalciferol.

The examples which follow further illustrate the disclosure.

EXAMPLE 1

| Item | Ingredients | mg/capsule | | |
|---|---|---|---|---|
| 1. | 25S,26-dihydroxycholecalciferol | 0.02 | 0.100 | 0.500 |
| 2. | polyethylene glycol 400 (PEG 400) | 200.00 | 200.00 | 200.00 |
| 3. | butylated hydroxy anisole (BHA) | 0.100 | 0.100 | 0.100 |
| 4. | ascorbyl palmitate | 1.00 | 1.00 | 1.00 |

Dissolve items 1, 3 and 4 in item 2, under a blanket of nitrogen and encapsulate.

EXAMPLE 2

| Item | Ingredients | | |
|---|---|---|---|
| 1. | 25S,26-dihydroxycholecalciferol | 0.10 mg | 0.50 mg |
| 2. | 95 ethanol-5% water | 2.00 ml | 3.00 ml |

Dissolve item 1 in item 2 under a blanket of nitrogen and inject intramuscularly.

We claim:

1. A method for the treatment of hypercalcitriolemic disease states which comprises administering an effective amount of 25S,26-dihydroxycholecalciferol to a host in need of such treatment.

2. A method in accordance with claim 1, wherein 25S,26-dihydroxycholecalciferol is administered in a dosage of about 20 to about 1000 micrograms per day.

3. A method in accordance with claim 1 for the treatment of hypercalcemic granulomatous disease which comprises administering an effective amount of 25S,26-dihydroxycholecalciferol to a host in need of such treatment.

4. A method in accordance with claim 3 wherein, 25S,26-dihydroxycholecalciferol is administered in an amount of about 20 to about 1000 micrograms per day.

5. A method for lowering the serum level of 1α,25-dihydroxycholecalciferol which comprises administering an effective amount of 25S,26-dihydroxycholecalciferol to a host in need of such treatment.

6. A method in accordance with claim 5, wherein 25S,26-dihydroxycholecalciferol is administered in an amount of about 20 to about 1000 micrograms per day.

7. A method in accordance with claim 1 for the treatment of inoperative primary hyperparathyroidism which comprises administering an effective amount of 25S,26-dihydroxycholecalciferol to a host in need of such treatment.

* * * * *